(12) United States Patent
Hughes et al.

(10) Patent No.: US 8,500,644 B2
(45) Date of Patent: Aug. 6, 2013

(54) APPLYING RENYI ENTROPY TO DETECT CHANGES IN SCATTERING ARCHITECTURE

(75) Inventors: Michael S. Hughes, St. Louis, MO (US); John McCarthy, St. Louis, MO (US); Gregory Lanza, St. Louis, MO (US); Mladen Victor Wickerhauser, St. Louis, MO (US); Samuel Wickline, St. Louis, MO (US)

(73) Assignee: Washington University, St. Louis, MO (US)

( * ) Notice: Subject to any disclaimer, the term of this patent is extended or adjusted under 35 U.S.C. 154(b) by 69 days.

(21) Appl. No.: 13/126,099

(22) PCT Filed: Oct. 28, 2009

(86) PCT No.: PCT/US2009/062322
§ 371 (c)(1),
(2), (4) Date: Apr. 26, 2011

(87) PCT Pub. No.: WO2010/062638
PCT Pub. Date: Jun. 3, 2010

(65) Prior Publication Data
US 2011/0208058 A1  Aug. 25, 2011

Related U.S. Application Data

(60) Provisional application No. 61/109,080, filed on Oct. 28, 2008.

(51) Int. Cl.
*A61B 8/00* (2006.01)
*G06K 9/00* (2006.01)

(52) U.S. Cl.
USPC ............ 600/443; 600/437; 600/438; 382/128

(58) Field of Classification Search
USPC .......................... 600/437, 443, 438; 382/128
See application file for complete search history.

(56) References Cited

U.S. PATENT DOCUMENTS

| 2004/0013292 | A1 | 1/2004 | Raunig |
| 2004/0022438 | A1* | 2/2004 | Hibbard .................... 382/199 |
| 2004/0059222 | A1 | 3/2004 | Nir |
| 2005/0244045 | A1 | 11/2005 | Eriksson |
| 2006/0257027 | A1* | 11/2006 | Hero et al. .................... 382/190 |
| 2007/0232909 | A1 | 10/2007 | Hughes et al. |

OTHER PUBLICATIONS

Flacke et al., "Novel MRI Contrast Agent for Molecular Imaging of Fibrin : Implications for Detecting Vulnerable Plaques", Circulation, 2001, pp. 1280-1285, vol. 104.
Lanza et al., "A Novel Site-Targeted Ultrasonic Contrast Agent with Broad Biomedical Application", Circulation, 1996, pp. 3334-3340, vol. 94.

(Continued)

*Primary Examiner* — Michael Rozanski
*Assistant Examiner* — Helene Bor
(74) *Attorney, Agent, or Firm* — Armstrong Teasdale LLP.

(57) ABSTRACT

A method for imaging a region of interest (ROI) within a body. The method includes applying ultrasound energy to the ROI, receiving ultrasound data for the ROI in response to the applied ultrasound energy, executing a moving window analysis on the received ultrasound data to generate a plurality of windows of information, applying a Renyi entropy signal receiver to each of the generated windows to generate Renyi entropy data, and presenting an image of the ROI based on the Renyi entropy data.

18 Claims, 16 Drawing Sheets

OTHER PUBLICATIONS

Arbeit et al., "Difluoromethylornithine Chemoprevention of Epidermal Carcinogenesis in K14-HPV16 transgenic mice", Cancer Research, 1999, pp. 3610-3620, vol. 59.

Arbeit et al., "Progressive Squamous Epithelial Neoplasia in K14-human Papillomavirus Type 16 Transgenic Mice", Journal of Virology, 1994, pp. 4358-4368, vol. 68, No. 7.

Hughes, "Analysis of digitized waveforms using Shannon entropy", Journal of the Acoustical Society of America, 1993, pp. 892-906, vol. 93, No. 2.

Hughes, "Analysis of digitized waveforms using Shannon entropy. II. high-speed algorithms based on Green's functions", Journal of the Acoustical Society of America, 1994, pp. 2582-2588, vol. 95, No. 5.

Hughes et al., "Real-time Calculation of a Limiting form of the Renyi Entropy Applied to Detection of Subtle Changes in Scattering Architecture" Aug. 26, 2008, Washington University School of Medicine, Department of Mathematics, Washington University, 6 pages.

Hughes et al., "Application of Renyi Entropy to Detect Subtle Changes in Scattering Architecture", Aug. 26, 2008, Washington University School of Medicine, Department of Mathematics, Washington University, 6 pages.

Seip et al., "Non-Invasive Detection of Thermal Effects due to Highly Focused Ultrasonic Fields", Department of Electrical Engineering and Computer Science, The University of Michigan, Ultrasonic Symposium, 1993, pp. 1229-1232.

Notification of transmittal of the International Search Report and the Written Opinion of the International Searching Authority, or the Declaration dated Jun. 1, 2010, for International Application No. PCT/US2009/062322; 12 pages.

\* cited by examiner

Renyi index of -1.00

Renyi index of 1.99

APPLYING RENYI ENTROPY TO DETECT CHANGES IN SCATTERING ARCHITECTURE

CROSS-REFERENCE TO RELATED APPLICATIONS

This application is a 35 U.S.C. §371 national stage application of PCT/US2009/062322, filed Oct. 28, 2009, which claims priority to U.S. Provisional Application No. 61/109,080, Oct. 28, 2008, the entireties of which are hereby incorporated by reference for all purposes.

BACKGROUND

Ultrasound has been used successfully as an imaging technology in diagnosis of breast, liver, prostate, rectal and pancreatic cancers. Conventionally, diagnosis with ultrasonic imaging typically requires a change in gross morphology of an underlying organ or a change in function, such as perfusion or blood velocity. With breast cancer, a size, shape, shadowing, internal echogenicity, lobulations, and other factors indicate a presence of a suspicious lesion. Commonly, lesions are then biopsied for ultimate confirmation of whether they are malignant or benign. Because many cancers can only be diagnosed by ultrasonic interrogation if those cancers are sufficiently extensive to alter the surrounding architecture, conventional ultrasonic imaging may overlook earlier stage cancers.

SUMMARY

In embodiments, described herein is a method for imaging a region of interest (ROI) within a body. The method includes applying ultrasound energy to the ROI, receiving ultrasound data for the ROI in response to the applied ultrasound energy, executing a moving window analysis on the received ultrasound data to generate a plurality of windows of information, applying a Renyi entropy signal receiver to each of the generated windows to generate Renyi entropy data, and presenting an image of the ROI based on the Renyi entropy data.

In further embodiments, described herein is an ultrasound imaging system. The system includes an ultrasound transducer configured to apply an acoustic signal to a region of interest (ROI) in a body, and transform a reflection of the applied acoustic signal into a raw radio frequency waveform. The system further includes an analog-to-digital converter (ADC) configured to generate a digitized waveform of the raw radio frequency waveform, and a processor configured compute pixel values from the digitized waveform, wherein a display device is configured to present an image of the ROI based on the pixel values.

BRIEF DESCRIPTION OF THE DRAWINGS

The present disclosure is described in detail below with reference to the attached drawing figure.

DETAILED DESCRIPTION

Figure 1:
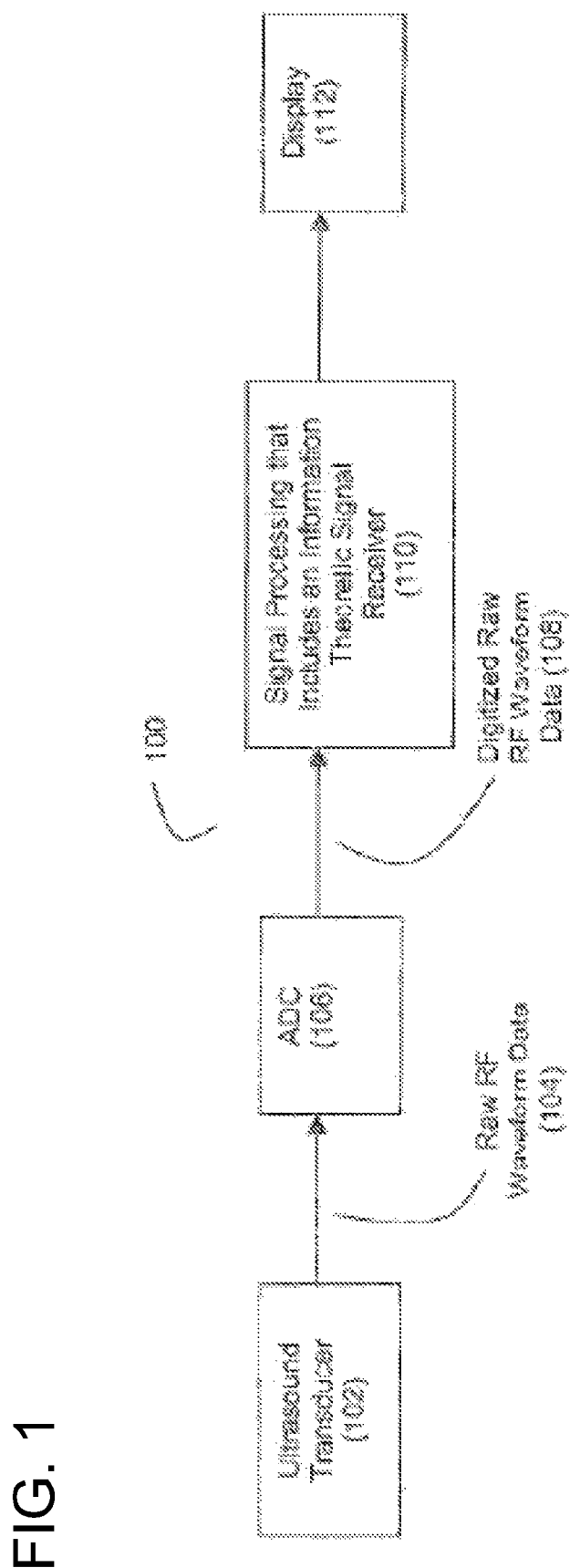
FIG. 1 illustrates a general block diagram of a system according to embodiments of the present disclosure.

Described herein is a use of Renyi entropy signal receivers as a basis for ultrasound imaging in not only high frequency ranges, but also lower frequency ranges such as those often employed in most clinical settings. Unexpected results in that detection of contrast-agent enhanced internal body conditions such as angiogenesis (e.g., nanoparticle-targeted angiogensis) can be achieved at clinical ultrasound frequencies when Renyi entropy signal receivers are applied to the radio frequency (RF) waveform produced by the ultrasound transducer. Further, both continuous entropy, $H_f$, and Renyi entropy, $I_f(r)$ of a continuous density function defined by Equation (1) below:

$$H_f = \int_{f_{min}}^{f_{max}} \rho_f(y)\log[\rho_f(y)]dy \ldots \quad (1)$$

$$I_f(r) = \frac{1}{1-r}\log\left[\int_{f_{min}}^{f_{max}} \rho_f(y)^r dy\right], \quad (1.1)$$

are more sensitive to accumulation targeted nanoparticles in pre-cancerous tissue conventional than are energy-based signal receivers. The mathematical structure of $\rho_f(y)$ ensures that Renyi Entropy-based signal characterization $I_f(r)$ becomes infinite as r→2. Thus, a difference in Renyi entropies of two subtly different wave forms f(t) and g(t) has potential to grow without bound as r→2. Furthermore, it currently takes weeks to compute a receiver value for typical clinical image data sets using previously developed algorithms. The present disclosure reduces the time to compute a receiver value for clinical image data sets to milliseconds.

A "signal receiver," in some embodiments, refers to an algorithm that is configured to transform an RF waveform or a portion thereof into a single datum (e.g., value or number). Such an algorithm can be implemented on a variety of devices (e.g., using software to be executed on a processor, using dedicated or reprogrammable hardware, or some combination thereof). The device that carries out this algorithm may be internal to or external to the ultrasound imaging system that is used to obtain the raw ultrasound RF waveform data. Examples of signal receivers that may be used in conventional ultrasound applications include total energy signal receivers, log of total energy signal receivers, and log of total energy signal receivers.

"Information theoretic" signal receivers are described in various publications. See U.S. Pat. Nos. 5,247,302, 5,280,291, and 5,392,046, the entire disclosures of each of which are incorporated herein by reference; see also Hughes, Michael S., A Comparison of Shannon entropy versus signal energy for acoustic detection of artificially induced defects in Plexiglas, J. Acoust. Soc. Am. 91(4), Pt. 1, pp. 2272-75, April 1992; Hughes, Michael S., Analysis of Ultrasonic Waveforms Using Shannon Entropy, 1992 Ultrasonics Symposium, pp. 1205-09, 1992; Hughes, Michael S., Analysis of digitized waveforms using Shannon entropy, J. Acoust. Soc. Am., 93(2), pp. 892-906, February 1993; Hughes, Michael S., Analysis of digitized waveforms using Shannon entropy. II. High-speed algorithms based on Green's functions, J. Acoust. Soc. Am., 95(5), Pt. 1, pp. 2582-88, May 1994, the entire disclosures of each of which are incorporated herein by reference.

Effective molecular imaging with ultrasound is highly desirable because ultrasound technology is clinically ubiquitous throughout the world, and because ultrasound technology is a comparatively cheap, portable, and straightforward imaging modality that is available at most medical centers. Accordingly, ultrasound technology offers an opportunity to implement clinical molecular imaging with global penetration as well as relevance to broad-based disease segments.

However, at lower ultrasound frequencies such as those available with most clinical ultrasound imaging equipment (e.g., frequencies in the range of approximately 2 MHz to approximately 15 MHz), it is generally believed that nanoparticle detection is less sensitive, especially for sparse concentrations of targets found in early cancers. This is a cause for concern as effective detection techniques at clinical ultrasound frequencies (relative to higher frequency research models) are desirable to more fully take advantage of ultrasound's global reach.

Use of contrast agents is a known technique to enhance a detection of cancers in conjunction with ultrasonic imaging. Contrast agents have been used to assist a detection of cancer in liver, prostate, and breasts. These contrast agents permit determination of perfusion properties of normal and cancerous tissue through, for example, an observation of wash-in and wash-out curves.

One molecular strategy for identifying solid cancers involves specific detection of molecular markers of tumor angiogenesis. It has been proposed that energetics of new cell growth associated with cancer demanded an energy source. Because means of delivering energy to and removing waste products from cancer cells are compromised near pathology, especially when tumor cells reach sizes greater than 1-2 $mm^3$, it is believed that there is a mechanism for cancer cells to alter their surrounding architecture to encourage new vessel growth. Previous studies have demonstrated an increase in new vessel growth ostensibly simulated by hypoxia in rapidly multiplying cancer cells that accompanies an "angiogenic switch" to a more aggressive phenotype capable of metastasis. The recruitment and formation of new vessels from surrounding vessels, otherwise known as angiogenesis, can provide a means of detecting early stage cancer by targeting angiogenic vessels or expressions of signaling and structural proteins associated with new vessel growth. A variety of proangiogenic signaling proteins have been examined as part of a cascade of reactions occurring to encourage new vessel growth.

For site-targeted nanoparticles applied at frequencies above 25 MHz, conventional ultrasonic backscatter as processed using known proprietary methods by ultrasound imaging devices has been shown to be sensitive to a presence of targeted nanoparticles, both in vitro and in vivo, especially when targets of the nanoparticles are abundant. Theoretical modeling indicates that these results may be understood to a rough first order approximation in terms of a simple transmission line model.

The combination of Renyi entropy signal receivers, $I_f(r)$, with administration of contrast agents provides marked enhancements to the detectability of internal pathologies such as angiogenesis. These improvements arise for a number of reasons. For example, unlike conventional ultrasound signal receivers (which are highly dependent upon the magnitude of the RF signal), Renyi entropy signal receivers are sensitive to the shape, i.e., undulations, of the RF waveform and are less signal-to-noise dependent. Moreover, Renyi entropy signal receivers are capable of effectively operating without a gating of input RF data, thereby providing an opportunity to eliminate operator dependence on results. Further still, because Renyi entropy signal receivers are employed after data acquisition, the present disclosure need not require a design and construction of new image acquisition systems. Moreover, the Renyi entropy signal receivers function well when a scattering object is near an interfacial boundary, which can be a significant issue in connection with a detection of angiogenesis, where tumor neovasculature vessels often bridge from an adjacent tissue border into the developing tumor capsule.

The application of heat to the contrast agent in conjunction with the use of Renyi entropy signal receivers can improve contrast enhancement for ultrasound imaging. In embodiments, the heat is a transient heat exhibiting a temperature that is nonlethal for cells subjected to the imaging. In further embodiments, this transient heating produces no cavitation (or negligible amounts of cavitation) in the region subject to the imaging.

In embodiments, other applications for the methodology, include, but are not limited to, detecting pathologies, monitoring tissue change over time, enhancing contact-facilitated drug delivery, and monitoring an effectiveness of contact-facilitated drug delivery.

FIG. 1 depicts an exemplary overview of an imaging system 100 capable of implementing embodiments of the present disclosure. In embodiments, the imaging system 100 is an ultrasound imaging system. However, other imaging modalities may be used in the practice of the present disclosure, including but not limited to magnetic resonance imaging, optical imaging, and nuclear imaging, as well as application to material characterization in a manufacturing environment, and for nondestructive evaluation of materials "in the field." Further, as set forth herein, the present disclosure is amenable to implementation with ultrasound imaging, both in vivo and in vitro. Additionally, the techniques of the present disclosure may be applied to areas such as intravascular imaging, transesophageal imaging, and acousto-optic imaging.

Figure 2:
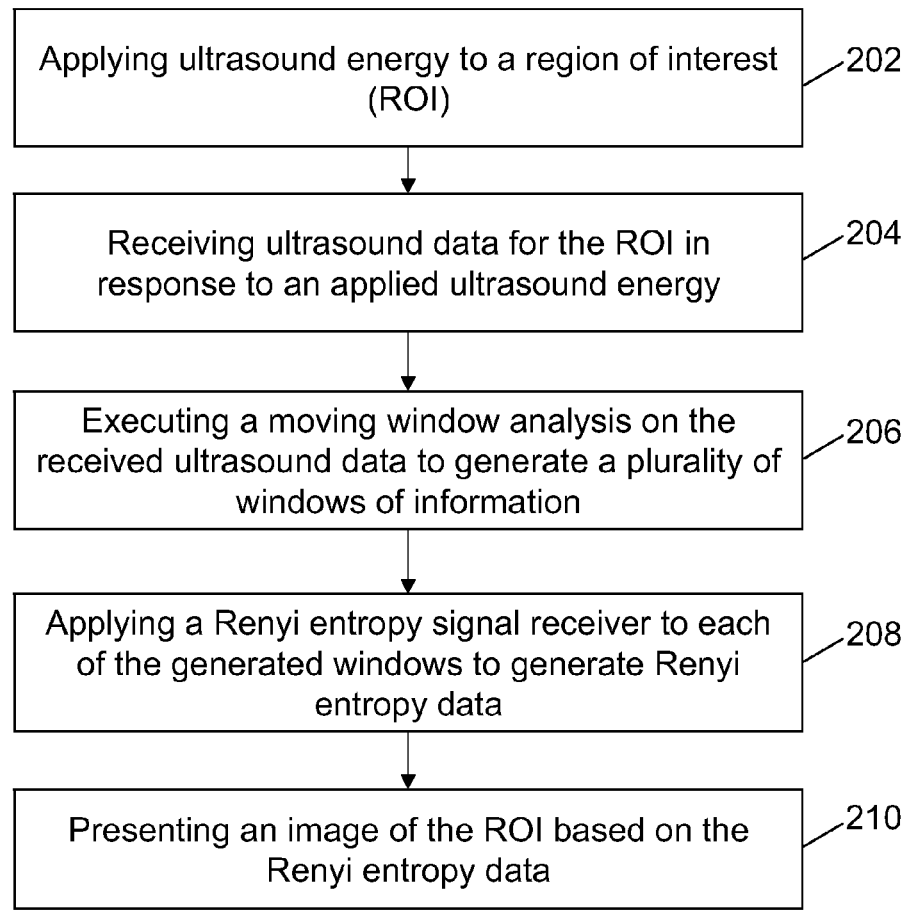
FIG. 2 illustrates a flow diagram of a method according to embodiments of the present disclosure.

FIG. 2 illustrates a flow diagram of a method according to embodiments of the present disclosure. At 202, an ultrasound transducer 102 is configured to apply an acoustic signal to a region of interest (ROI) and at 204 receive acoustic reflections that are transformed into raw RF waveform data 104 that is representative of an interaction of the acoustic signal with the ROI. This raw RF waveform data 104 is then processed through an analog-to-digital converter (ADC) 106 that digitizes the raw RF waveform produced by the transducer 102.

In one embodiment, the ultrasound system can be a research imager such as a Vevo 660 ultrasound system available from Visualsonics of Toronto, Canada with a 30 MHz single element "wobbler" probe/transducer configured to acquire the raw waveform data in a B-scan format, as is known in the art. However, any of a number of commercially-available or custom-designed ultrasound acquisition systems can be used in the practice of the present disclosure, including clinical ultrasound systems that operate at lower frequencies than do higher end research models, such as the Philips IE33 Ultrasonic Medical imaging system. In embodiments, the ultrasound transducer 102 acquires RF data in a B-scan format at select times (e.g., pre-injection and at 0, 15, 30, 60, and 120 minutes after injection of a contrast agent into the area of interest).

The ADC 106 is configured to sample the raw waveform 104 at a predetermined sampling rate (such as 500 MHz) to generate a digitized waveform 108 that comprises multiple frames, each of which comprises a plurality of lines of numerous multi-bit words. Each frame corresponds spatially to an area within the ROI.

At 206, a processor 110 that includes a Renyi entropy signal receiver operates to receive and process the digital data 108 to compute pixel values, for example, by performing a "moving window" analysis of each digitized waveform. Thereafter, images corresponding to computed pixel values can be shown on a display 112 such as a screen of a computer monitor or the like. In embodiments, the image will be capable of indicating whether a condition of interest exists within the ROI with greater precision than conventional ultrasound images that are processed using the conventional total energy or log (total energy) signal receivers that are known in the art. Examples of conditions of interest that can be gauged by the practice of the present disclosure include angiogenesis (in various conditions such as solid tumor growth (VX2 tumors, MDA435 tumors, etc.) and metastasis, cancer, diabetic retinopathy, macular degeneration, muscular dystrophy or atherosclerosis due to expansion of the vasa vasorum under high cholesterol drive), blood clots (in arteries, veins, heart chambers, aorta or on valves), small deposits of fibrin or platelets on unstable atherosclerotic plaque, and small collections of tumor cells in accessible parts of the body to name just a few. The processor 110 can be any commercially-available processor having sufficient computing power to carry out the operations described herein.

With respect to targeted contrast agents, examples include contrast agents that are targeted to $\alpha_v\beta_3$ in angiogenic vessels, contrast agents that are targeted to fibrin in atherosclerotic placques, contrast agents that are targeted to fibrin in thrombi, and contrast agents that are targeted to tissue factor in blood vessel walls or in tumors. A preferred targeted contrast agent for use in the present disclosure comprises lipid-encapsulated, liquid perfluorocarbon nanoparticles that are approximately 200-250 nm in diameter. The nanoparticles can be loaded with gadolinium to achieve MRI contrast, while the perfluorocarbon liquid interior of the agent simultaneously provides acoustic contrast. These particles have been successfully targeted to a variety of molecular markers for imaging with either or both ultrasound and MRI.

The ultrasound transducer 102 is preferably used to apply ultrasound energy in the form of an acoustic wave to the ROI. Because of the sensitivity provided by the Renyi entropy signal receivers, this energy can be applied at frequencies much lower than the high "research" ultrasound frequencies (e.g., 25 MHz or above). When Renyi entropy signal receivers are used in conjunction with targeted contrast agents and ultrasound imaging to detect conditions such as angiogenesis, effective imaging results can be obtained at intermediate frequencies (e.g. 7-15 MHz) with clinical imaging equipment, and even at low frequencies (e.g., 2-4 MHz) with clinical imaging equipment. The ability to effectively image conditions such as angiogenesis at lower frequencies with the techniques of the present disclosure arises from Renyi entropy signal receivers' sensitivity to diffuse, low amplitude features of the RF signal that are often otherwise obscured by noise or hidden in large specular echoes.

In embodiments, the ultrasound transducer 102 senses the reflected acoustic wave and produces as an output the raw RF waveform voltages 104 from which the images will be produced. In further embodiments, the ultrasound transducer operates in B-scan mode. However, it should be noted that A mode and M mode data can be used. Furthermore, the ultrasound transducer 102 may be any of a variety of known ultrasound transducer configurations, including a single transducer, an array of transducers, and a wobbler medical imaging probe.

In embodiments, ADC 106 samples raw waveform at a predetermined sampling rate (such as 500 MHz) to generate digitized raw RF waveform data 108 that comprises a plurality of frames, each frame comprising a plurality of lines, each line comprising a plurality of multi-bit words whose values correspond to pixel values. For example, a frame may comprise 384 lines of 4096 8-bit words/pixels. However, it should be readily understood that other frame sizes could be used in the practice of the disclosure.

In embodiments, the digitized waveform data 108 is upsampled, using for example, a cubic spline, or any other suitable fitting procedure fit to the digitized rf data in order to stabilize the information Renyi entropy signal receiver algorithms, which benefit from increased waveform length. In further embodiments, a moving window analysis is performed on the receiving ultrasound data. With a moving window analysis, (1) a plurality W of consecutive points (which can also be referred to as words or pixels) in the waveform are selected starting from the first point to generate the first window position, (2) another W consecutive points in the waveform are selected starting from point S in the waveform to generate the second window position, (3) another W consecutive points in the waveform are selected starting from point 2S in the waveform to generate the third window position, and (4) this process is repeated until it is no longer possible to select W consecutive points in the waveform data without going past the last point in the waveform data. Thus, the moving window analysis involves iteratively selecting a defined plurality of consecutive points to generate a window position until each of the points in the digitized waveform has been included in a window. The W consecutive points can be referred to as the windowed points (or words/pixels) since they may be thought of as having been obtained by applying a square wave window to the entire digital waveform and taking the nonzero points of the resulting windowed waveform. In some embodiments, the consecutive points are adjacent points, successive points, or otherwise in order. As this selection of windowed points is made at successively greater delays into the entire digital waveform, this process may be thought of as having been performed by sliding a square gating function over the entire digital waveform, hence the term sliding window analysis. Exemplary values for W and S are 64 and 32 respectively, but it should be readily understood that other positive integer values for W and S could be used in the practice of the present disclosure (e.g., particularly other powers of 2). For example with the 384 line/8192 word example used herein, this moving window analysis can use a window having a word length W of 64 words that is moved in 0.064 μs steps (or a stepsize S of 64 words), thereby resulting in 128 window positions within the original data set.

Next, at 208 the generated values of the windowed words within each window position are input into a Renyi entropy signal receiver to compute the single datum for each window position. In embodiments, each datum then serves as a pixel in a resulting information theoretic (IT) image. Thus, the IT image for the 384 line/8192 word example might have 384×128 pixels whose values are the single values computed by the information theoretic signal receiver for each of the window positions, depending on the length of the moving window used for the analysis.

Renyi entropy signal receivers analyze the statistical distribution of digitized voltage levels from an acoustic signal and are highly sensitive to diffuse, low amplitude features of the signal that are often obscured by noise or lost in large specular echoes.

Next, the $I_f(r)$ image data may be used to compute a cumulative distribution function (CDF) for pixel values in the $I_f(r)$ image. Pixels in CDF can then be thresholded at some percentage (such as the upper 5% of pixel values) to segment an $I_f(r)$ image into regions corresponding to targeted areas and non-targeted areas. The choice of a specific threshold value is a design parameter that can be varied by practitioners of the disclosure to suit a given application. Moreover, pixels falling above or below the threshold can be color-coded in the image to render targeted areas more clearly. Further still, the use of such a CDF analysis of normalized pixel values enables a comparison between images and/or a combination of images that were created with different signal receivers and different physical units. Thus, effective comparisons can be made between two images that were created using different signal receivers (such as one image created with an Renyi entropy signal receiver and another image created with a conventional signal receiver, or one image created with a first type of Renyi entropy receiver, e.g., $I_f(r)$ with r=1.99, and a second image created with a second type of Renyi entropy signal receiver, e.g., $I_f(r)$ with r=1.5).

Also, the pixels that are above (or below depending on the application) the brightness threshold (such as the upper 5% of pixels can be combined with the pixels of a conventional image, wherein the pixels of the conventional image that are coextensive with the pixels passing the threshold are replaced by the brightest 5% of the information theoretic signal receiver-enhanced pixels. The Renyi entropy signal receiver-enhanced pixels can then be color-coded to clearly delineate the contrast enhanced area, and at 210, an image of the ROI based on the Renyi entropy datum can be presented to a user via a display device.

In embodiments, the steps herein may be repeated over time to generate a plurality of images that would track the enhancement provided by the contrast agent over time. For example, the steps can be performed at 0, 15, 30, 60, and 120 minutes post-injection of contrast agent. Further still, when used to monitor a condition such as angiogenesis, the steps can be repeated over longer intervals of time to monitor angiogenic development by quantifying changes in the ROI over time.

Data

An entropy-based signal receiver is more sensitive to subtle changes in scattering architecture than conventional energy-based signal characterization. Described herein are improvements in sensitivity using a signal receiver based on Renyi entropy.

With respect to a Shannon Entropy analog, $H_f$ and more conventional signal processing techniques, i.e., signal energy and its algorithm as applied to beam formed radiofrequency (RF) data, both analysis techniques may be applied to data obtained in backscatter measurements from nanoparticle targeted neovasculature. A comparison study was undertaken after a preliminary conventional B-mode grayscale analysis of data was unable to detect changes in backscattered RF arising from the accumulation of targeted nanoparticles in the neovasculature in the insonified region. This result implied that acoustic characterization of sparse collections of targeted perfluorocarbon nanoparticles presented challenges that might require the application of novel types of signal processing. Signal processing, based on a "moving window" $H_f$ analysis, may distinguish the difference in backscatter measured at 15 and 60 minutes and (although it was not stressed) able to detect accumulation of targeted nanoparticles 30 minutes post-injection. The signal energy, defined as the sum of squares of the signal amplitude over the same moving window, was unable to distinguish measurements made at any time during the one hour experiment.

Further, it was demonstrated that a signal characterization using entropy, $H_f$, in certain settings, further improves signal characterization could be obtained by generalizing to Renyi Entropy-based signal characterization, $I_f(r)$ with values of r near 2 (specifically r=1.99) It was speculated that further improvements in sensitivity might be realized at the limit r→2. In the present disclosure, an asymptotic expression, $I_{f,\infty}$, for the limiting behavior of $I_f(r)$ as r→2 is derived and results are presented analogous to those obtained with $I_f$ (1.99). Moreover, the limiting form, $I_{f,\infty}$ is computable directly from the experimentally measured waveform, f(t) by an algorithm suitable for real-time implementation.

In embodiments, the application of Renyi entropy, $I_f(r)$, which is defined for all r<2, for the detection of changes in backscattered RF arising from the accumulation of targeted nanoparticles in the neovasculature in the insonified region of a tumor may be shown. In further embodiments, signal processing may be shown based on a "moving window" $H_f$ analysis could distinguish the difference in backscatter measured at 15 and 60 minutes post-injection and (although it was not stressed) able to detect accumulation of targeted nanoparticles 30 minutes post-injection. The signal energy, defined as a sum of squares of over the same moving window, was unable to distinguish measurements made at any time during the one hour experiment (as was conventional B-node imaging). Subsequently, it is determined that a "moving window" $I_f(r)$ analysis, with r=1.99, can distinguish the difference in backscatter measured at 0 and 15 minutes. Reduction of the accumulation time required to reach detectability from 30 to 15 minutes is clearly of clinical significance. Moreover, although the computational effort to obtain the result precluded its clinical application with currently available equipment, the study raised the possibility of further sensitivity improvements by using values of r closer to the limiting value of 2, where $I_f(r)$ is approaching infinity.

Signal analysis based on $H_f$, $I_f(1.99)$ and $I_{f,\infty}$, is capable of detecting differences between digital signals that are undetectable by conventional methods of characterization based on peak-to-peak amplitude or signal energy. Applying these quantities to a problem from nondestructive materials evaluation, i.e., detection of foreign objects (FO) embedded near the surface of thin graphite/epoxy laminates using backscattered waveforms obtained by C-scanning the laminate, show that $H_f$, $I_f$ (1.99) and $I_{f,\infty}$ are able distinguish waveforms acquired from the region containing the FO from those acquired outside. $H_f$, $I_f$ (1.99) and $I_{f,\infty}$, exhibit significant increases (e.g., up to 20-fold) in contrast and for certain types of FO materials permit detection when energy or amplitude methods fail altogether.

In embodiments, all RF data are obtained by sampling a continuous function, y=f(t), and subsequently using the sampled values to compute its associated density function, $\rho_f(y)$.

The density function $\rho_f(y)$ may be used to compute the entropy $H_f$. It corresponds to the density functions used in statistical signal processing. From it other mathematical quantities are subsequently derived (e.g., mean values, variances, covariances)[3-5]. While the density function is usually assumed to be continuous, infinitely differentiable, and to approach zero at infinity in statistical signal processing of random signals, in our application $\rho_f(y)$ has (integrable) singularities.

The convention that the domain of f(t), is [0,1] may be adopted so that, $\rho_f(y)$, the density function of f(t), can be defined by the basic integral relation:

$$\int_0^1 \phi(f(t))dt = \int_{fmin}^{fmax} \phi(y)\rho_f(y)dy, \quad (1.5)$$

Equation (1.5) implies:

$$\rho_f(\xi) = \sum_{\{t_k | f(t_k) = \xi\}} \frac{1}{|f'(t_k)|} \quad (2)$$

either by breaking the integral into a sum over intervals of monotonicity of f(t) ("laps") and changing variables, or by choosing $\phi(y)$ to be a Dirac delta function and using the well-known expansion formula for a delta function of a function. Where: f(t) is the underlying continuous waveform which is sampled during the measurement process; $\rho_f(y)$ is the density function of the underlying continuous waveform, f(t), that is, it measures how long f(t) spends at each of its values:

$$\rho_f(y) = \sum_{k=1}^{N} |g'_k(y)|; \quad (2.5)$$

and $t_k$ is the time at which the $k^{th}$ critical point (i.e., $f'(t_k)=0$, that happens when f(t) attains a maxima or minima) occurs]. It will be assumed that digitizable waveforms f(t) are comprised of at least one section, or "lap," where it is monotonic. The lap boundaries are the points t where $f'(t)=0$. On each lap, f(t) has a well-defined inverse function. These may be used to rewrite Equation (2):

$$\rho_f(y) = \sum_{k=1}^{N} |g'_k(y)| \quad (3)$$

where N is the number of laps, $g_k(y)$ is the inverse of f(t) in the $k^{th}$-lap, and if y is not in the range of f(t) in the $k^{th}$-lap, $g'_k(y)$ is taken to be 0.

In embodiments, for experimentally measured data, it may also be assumed that digitizable waveforms f(t) have a Taylor series expansion at points in [0,1]. Then near a time $t_k$ such that $f'(t_k)=0$ $$y = f(t) = f(t_k) + \frac{1}{2!} f''(t_k)(t-t_k)^2 + \ldots, \quad (4)$$

$t_k$ is a lap boundary and on the left side of this point Equation (4) may be truncated to second order and inverted to obtain:

$$g_k(y) \sim t_k \pm \sqrt{2(y-f(t_k))/f''(t_k)}, \quad (5),$$

with $$|g'_k(y)| \sim 1/\sqrt{2f''(t_k)(y-f(t_k))}, \quad (6)$$

The contribution to $\rho_f(y)$ from the right side of the lap boundary, from $g_{k+1}(y)$, is the same, so that the overall contribution $\rho_f(y)$ coming from the time interval around $t_k$ is:

$$|g'_k(y)| \sim \sqrt{2/(f''(t_k)(y-f(t_k)))}, \quad (7)$$

for $0<f(t_k)-y<<1$ for a maxima at $f(t_k)$ and $0<y-f(t_k)$ for a minima. Thus, $\rho_f(y)$ has a square root singularity (assuming that $t_k$ is interior to the interval [0,1], if not, then the contributions to $w_f$ come from only the left or the right). If additionally, $f''(t_k)$ then the square root singularity in Equation (6) will become a cube-root singularity, and so on, so that the density functions considered will have only integrable algebraic singularities.

Figure 3:
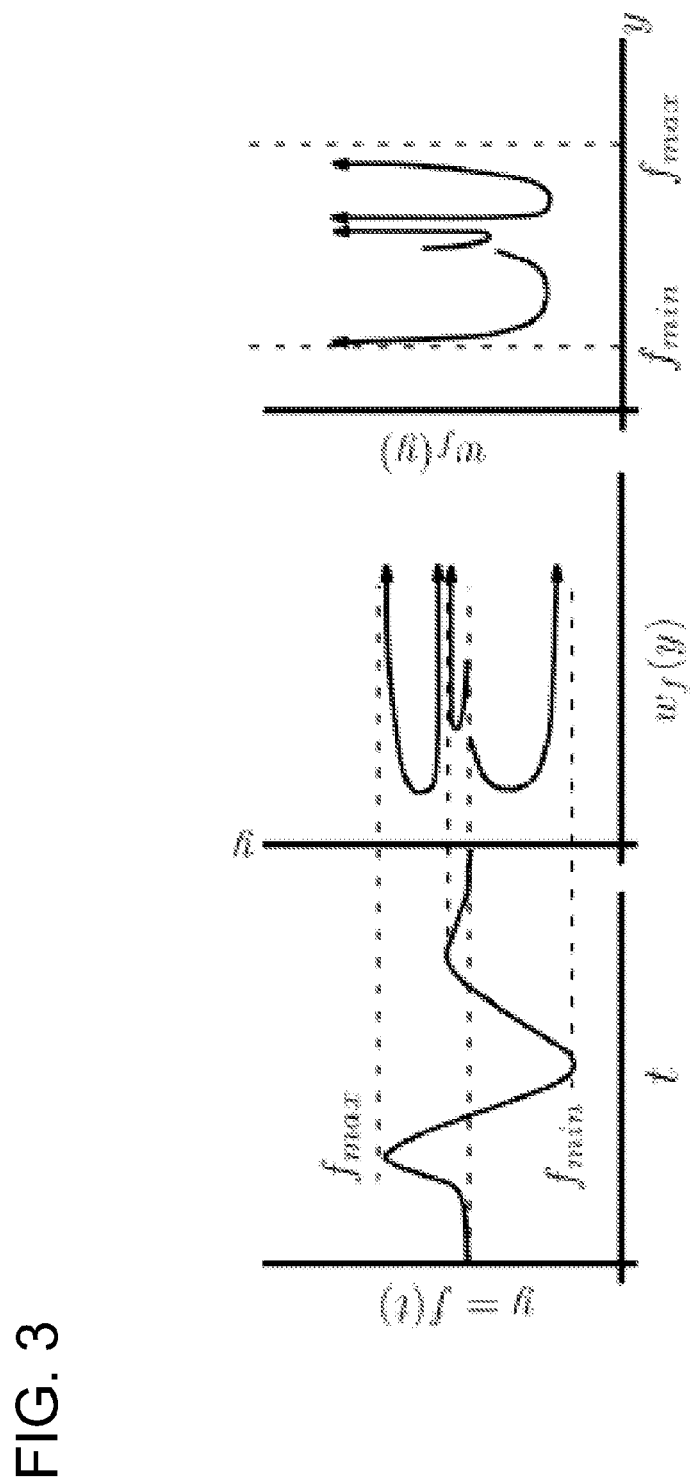
FIG. 3 illustrates a time-domain waveform.

FIG. 3 illustrates, schematically, two types of behavior possible in $\rho_f(y)$: both discontinuities and algebraic singularities (indicated by arrows on the plots of $w_f(y)$). Progressing from left to right in FIG. 3 illustrates how to estimate qualitative features of $\rho_f(y)$ from f(t). For instance, in embodiments, the maxima in f(t) correspond to an algebraic singularities in $\rho_f(y)$ plotted sideways in the middle panel to more clearly indicate the relationship between its features and those of f(t). The rightmost panel shows $\rho_f(y)$ in a conventional layout (a rotated and flipped version of the plot in the middle panel). These plots show that the density functions possess significantly different attributes from those usually considered in statistical signal processing.

The mathematical characteristics of the singularities are important in order to guarantee the existence of the following integral on which the analysis of signals in the study is based:

$$I_f(r) = \frac{1}{1-r} \log \left[ \int_{fmin}^{fmax} \rho_f(y)^r dy \right], \quad (8)$$

which known as the Renyi entropy and which is similar to the partition function in statistical mechanics with the parameter r playing the role of a reciprocal temperature, moreover, $I_f(r) \to H_f$ as $r \to 1$, using L'Hopital's, so that $I_f$ is a generalization of $H_f$:

$$H_f = \int_{fmin}^{fmax} \rho_f(y) \log[\rho_f(y)] dy, \quad (9)$$

This quantity can be more sensitive to subtle changes in scattering architecture than more commonly used energy-based measures. Thus, described herein are sensitivity improvements using $I_f(r)$ at the suitable value of r.

In embodiments, for the density functions $w_f(y)$, $I_f(r)$ is undefined for $r \geq 2$, since as $r \to 2^-$. Moreover, as $r \to 2^-$, the integral appearing in Equation (8) may grow without bound due to the singularities in the density function, $\rho_f(y)$ described in Equation (6). The behavior as $r \to 2$ is dominated by contributions from the singularities. If the $k^{th}$ critical point is a minima (the argument for a maxima is similar) the contribution to the integral in Equation (8) is asymptotic to:

$$\lim_{\epsilon \to 0} \int_{f(t_k)}^{fmax} \left( \frac{a_k}{\sqrt{y - f(t_k)}} \right)^{2-\epsilon} dy. \quad (10)$$

This is equal to:

$$= \lim_{\epsilon \to 0} a_k^{2-\epsilon} \int_{f(t_k)}^{fmax} (y - f(t_k))^{1-\epsilon/2} dy, \quad (11)$$

-continued $$= \lim_{\epsilon \to 0} a_k^{2-\epsilon} \frac{(y-f(t_k))^{\epsilon/2}}{\epsilon/2} \Big|_{f(t_k)}^{f_{max}},$$

$$= \lim_{\epsilon \to 0} a_k^{2-\epsilon} \frac{(f_{max}-f(t_k))^{\epsilon/2}}{\epsilon/2},$$

$$= \lim_{\epsilon \to 0} \frac{2 a_k^2}{\epsilon},$$

Where $\alpha_k = \sqrt{2/f''(t_k)}$.

Aside: for a maxima, the asymptotic term is present:

$$\lim_{\epsilon \to 0} \int_{f_{min}}^{f(t_k)} \left( \frac{a_k}{\sqrt{f(t_k)-y}} \right)^{2-\epsilon} dy. \quad (12)$$

This is equal to:

$$= \lim_{\epsilon \to 0} a_k^{2-\epsilon} \int_{f_{min}}^{f(t_k)} (f(t_k)-y)^{1-\epsilon/2} dy, \quad (13)$$

$$= \lim_{\epsilon \to 0} a_k^{2-\epsilon} \frac{(f(t_k)-y)^{\epsilon/2}}{\epsilon/2} \Big|_{f_{min}}^{f(t_k)},$$

$$= \lim_{\epsilon \to 0} a_k^{2-\epsilon} \frac{(f(t_k)-f_{min})^{\epsilon/2}}{\epsilon/2},$$

$$= \lim_{\epsilon \to 0} \frac{2 a_k^2}{\epsilon},$$

where now have a different expression for $\alpha_k = \sqrt{2/f''(t_k)}$.

Figure 4:
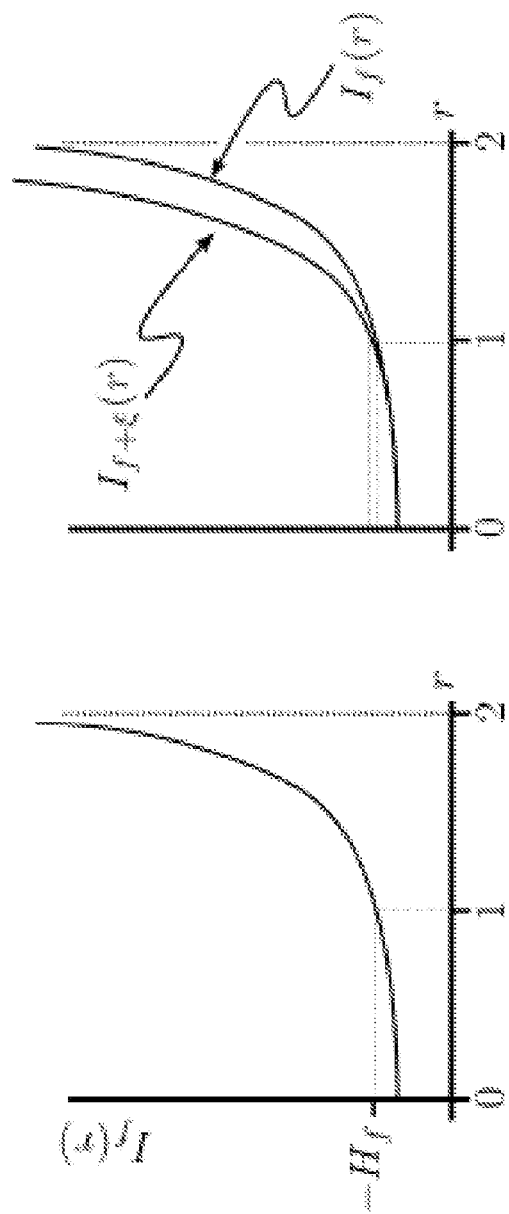
FIG. 4 illustrates a left panel and a right panel.

This behavior is shown in the left panel of FIG. 4. Moreover, as shown in the right panel, it is possible that two slightly different functions, f(t) and f(t)+ξ(t), where ξ is small, may have entropies, $H_f$ and $H_{f+\xi}$, that are close, as shown in FIG. 4, but whose Renyi entropies, $I_f(r)$ diverge as $I_{f+\xi}(r)$. Thus, if this amplification effect were not dominated by noise, it permits separation of subtly different functions, such as those obtained from measurements of backscattered ultrasound of targeted and nontargeted tissue.

In embodiments, for in vivo imaging, nanoparticles targeted to $\alpha_v\beta_3$-integrins of neovascularity in cancer are formulated by incorporating an "Arg-Gly-Asp" mimetic binding ligand into the lipid layer. Methods were used to prepare perfluorocarbon (perfluorooctylbromide, PFOB, which remains in a liquid state at body temperature and at the acoustic pressures used herein emulsions encapsulated by a lipid-surfactant monolayer. The nominal sizes for each formulation may be measured with a submicron particle analyzer, with a particle diameter measured at 200±30 nm.

The model used is the transgenic K14-HPV16 mouse in which the ears typically exhibit squamous metaplasia, a precancerous condition, associated with abundant neovasculature that expresses the $\alpha_v\beta_3$ integrin. Eight of these transgenic mice were treated with 1.0 mg/kg i.v. of either $\alpha_v\beta_3$-targeted nanoparticles (n=4) or untargeted nanoparticles (n=4) and imaged dynamically for one hour using a research ultrasound imager (Vevo 660 40 MHz probe) modified to store digitized RF waveforms acquired at 0, 15, 30, and 60 minute time points. In both targeted and untargeted cases, the mouse was placed on a heated platform maintained at 37° C., and anesthesia was administered continuously with isoflurane gas (0.5%).

Figure 5:
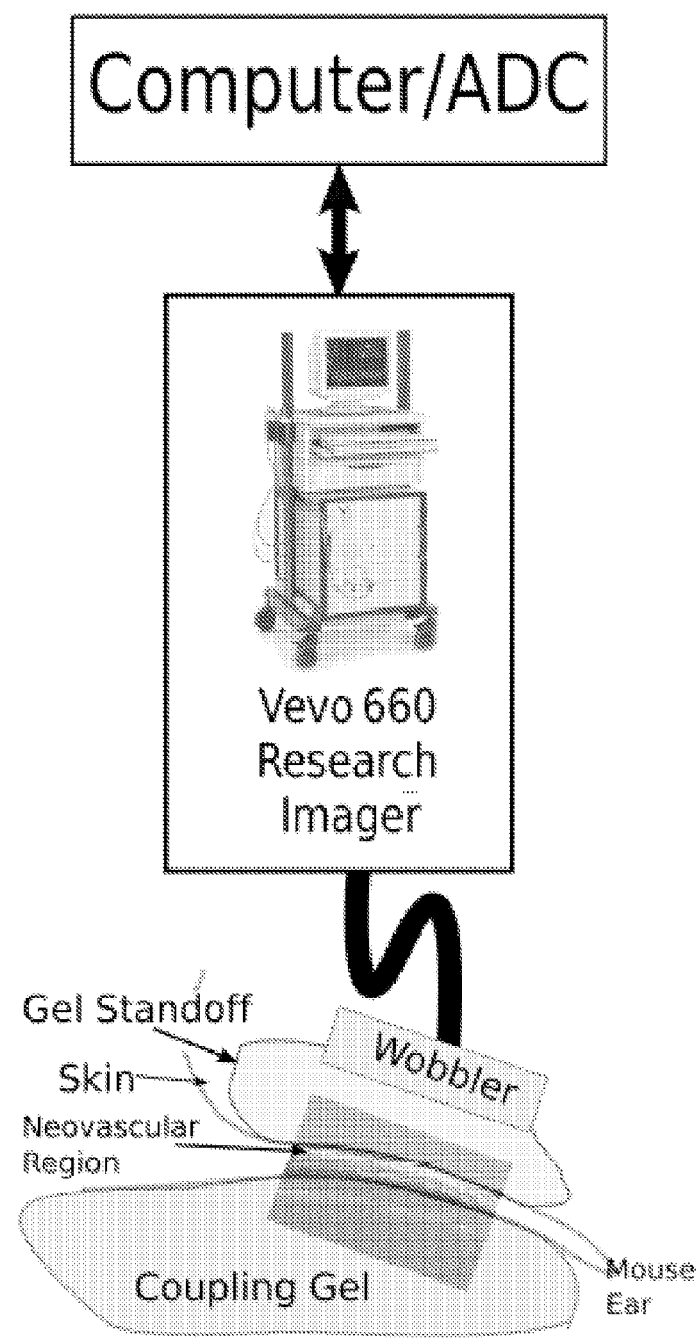
FIG. 5 illustrates a diagram of an apparatus used to acquire RF data.

A diagram of an apparatus for use in implementing embodiments of the present disclosure is shown in FIG. 5.

Radio-frequency (RF) data were acquired with a research ultrasound system (Vevo 660, Visualsonics, Toronto, Canada), with an analog port and a sync port to permit digitization. The tumor may be imaged with a 40 MHz single element "wobbler" probe and the RF data corresponding to single frames were stored on a hard disk for later off-line analysis. The frames (acquired at a rate of 40 Hz) may be consisted of 384 lines of 4096 eight-bit words acquired at a sampling rate of 500 MHz using a Gage CS82G digitizer card (connected to the analog-out and sync ports of the Vevo) in a controller PC. Each frame may correspond spatially to a region about 0.8 cm wide and about 0.3 cm deep.

The wobbler transducer used may be highly focused (3 mm in diameter) with a focal length of about 6 mm and a theoretical spot size of about 80×1100 μm (lateral beam width x depth of field at −6 dB), so that the imager is sensitive to changes occurring in the region swept out by the focal zone as the transducer is "wobbled." Accordingly, a gel standoff may be used, as shown in FIG. 5, so that this region would contain the mouse ear.

A close-up view showing the placement of transducer, gel standoff, and mouse ear is shown in the bottom of FIG. 5. Superposed on the diagram is a B-mode gray scale image (i.e., algorithm of the analytic signal magnitude). Labels indicate the location of skin (top of image insert), the structural cartilage in the middle of the ear, and a short distance below this, the echo from the skin at the bottom of the ear. Directly above this is an image of a histological specimen extracted from a HPV mouse model that has been magnified 20 times to permit better assessment of the thickness and architecture of the sites where $\alpha_v\beta_3$ targeted nanoparticle might attach (red by $\beta_3$ staining) Skin and tumor are both visible in the image. On either side of the cartilage (center band in image), extending to the dermal-epidermal junction, is the stroma. It is filled with neoangiogenic microvessels. These microvessels are also decorated with nanoparticles as indicated by the fluorescent image of a bisected ear from an $\alpha_v\beta_3$-injected K14-HPV16 transgenic mouse. It is in this region that the $\alpha_v\beta_3$-targeted nanoparticles are expected to accumulate, as indicated by the presence of red $\beta_3$ stain in the magnified image of a histological specimen.

Each of the 384 RF lines in the data may be first up-sampled from 4096 to 8192 points, using a cubic spline fit to the original data set in order to improve the stability of the thermodynamic receiver algorithms. As a by-product of this "order n" algorithm is simultaneous output of a corresponding array of array second derivative values of the fit function. In embodiments, increased input waveform length may be beneficial. In further embodiments, a moving window analysis may be performed on the upsampled data set using a rectangular window that was advanced in 0.064 μs steps (64 points), resulting in 121 window positions within the original data set. This was done using both continuous entropy, $H_f$ and Renyi entropy $I_f(1.99)$ analysis of the RF segments within each window in order to produce an image (either $H_f$ or $I_f$ (1.99)) for each time point in the experiment. As described previously, the density function, $\rho_f(y)$ used to compute $H_f$ and $I_f(1.99)$ is computed using a Fourier series representation. For this study, where the desire was to compute $I_f(r)$ as near to its singular value as possible, it was found that 16384 terms were required for accurate estimation. In order to complete computations in a reasonable amount of time all calculations where performed on a linux cluster using Open MPI.

RF data may be processed off-line to reconstruct $I_{f\infty}$ images using information theoretic, either $H_f$ or $I_f$ (1.99). Subsequently, a histogram of (either either $H_f$ or $I_f$ (1.99)) pixel values for the composite of the 0, 15, 30, and 60 minute images may be computed, either $H_f$ or $I_f$(1.99). Image segmentation of each type of image, either $H_f$ or $I_f$(1.99), at each time point in the example was then performed automatically using its corresponding histogram according to the following threshold criterion: the lowest 7% of pixel values were classified as "targeted" tissue, while the remaining were classified as "untargeted" (histogram analysis was also performed using 10 and 13 percent thresholds, with 7% having better statistical separation between time points). The mean value of pixels classified as "targeted" was computed at each time post-injection.

Figure 6:
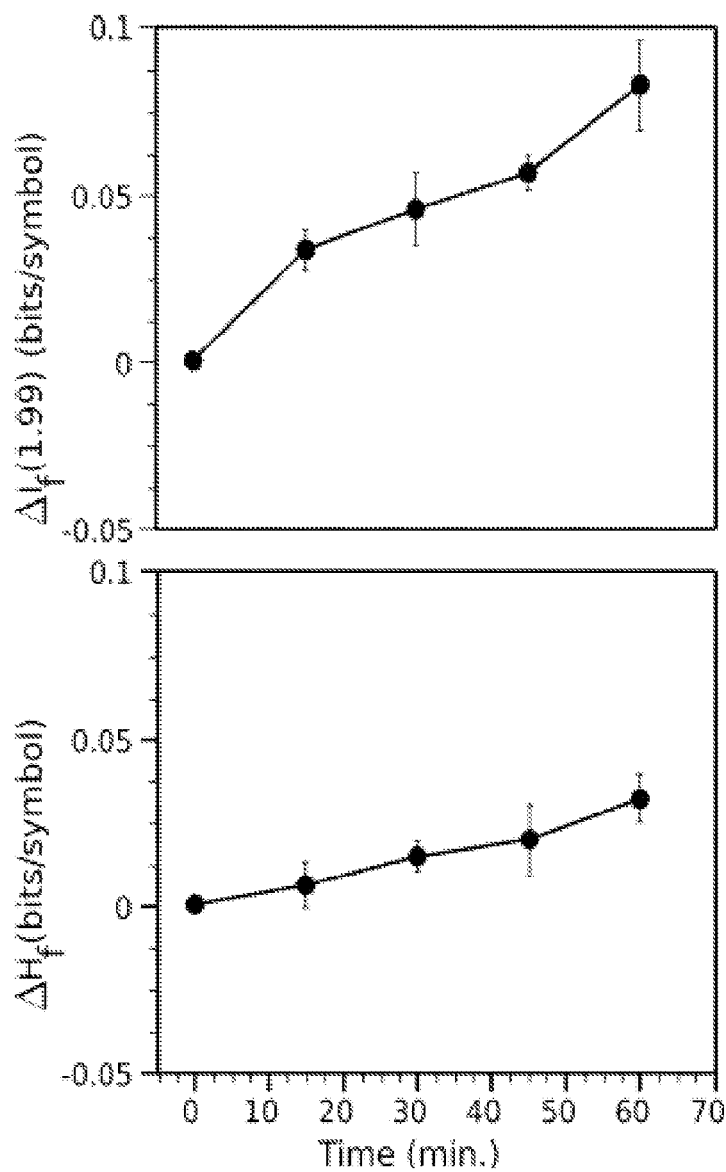
FIG. 6 illustrates a plot average enhancement.

The results obtained after injection of targeted nanoparticles, by either the $H_f$ or $I_f$(1.99) receivers, are shown in the top and bottom panels of FIG. 6. Both panels compare the growth, with time, of the change (relative to 0 minutes) in mean value of receiver output in the enhanced regions of images obtained from all four of the animals in the targeted group. Standard error bars are shown with each point. At fifteen minutes, the change in mean value if $I_f$(1.99) is more than two standard errors from zero, implying statistical significance at the 95% level. As the bottom panel shows it is 30 minutes before $H_f$ is more than twice the standard error from zero.

Figure 7:
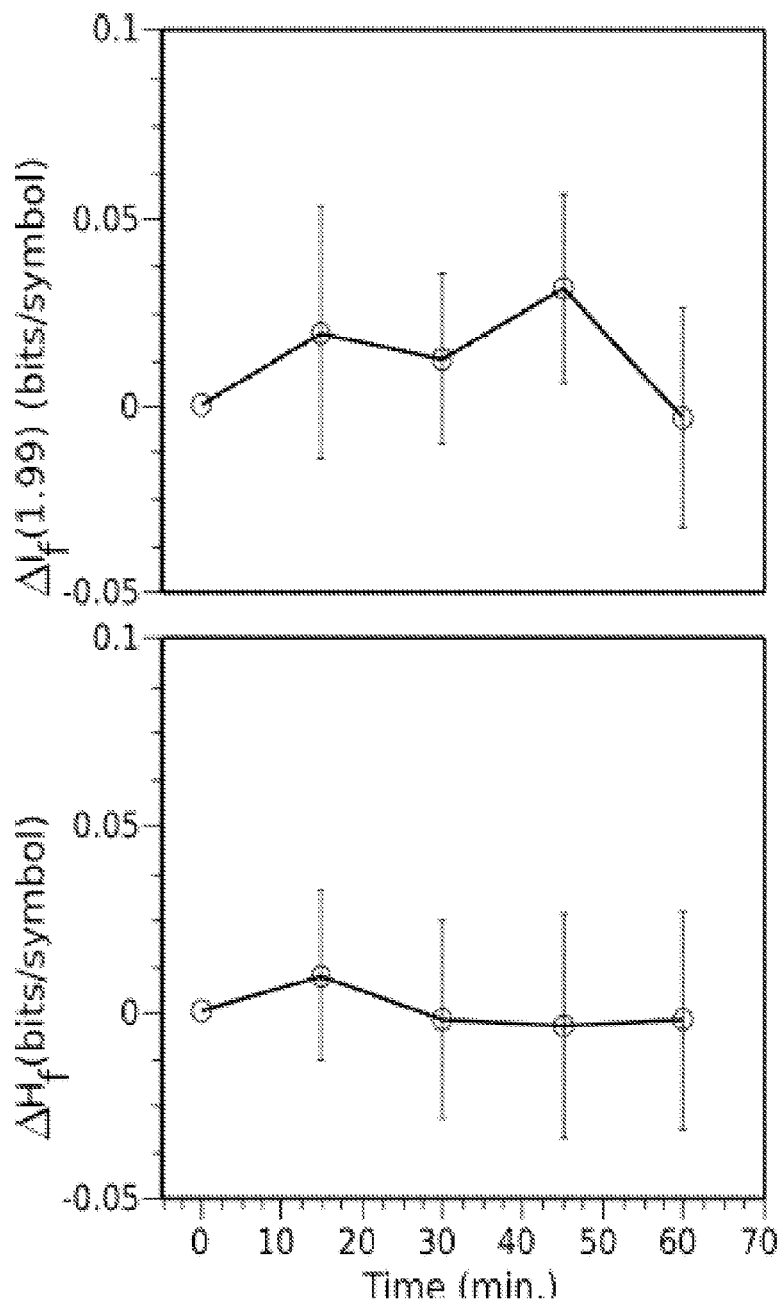
FIG. 7 illustrates a plot average enhancement.

The results obtained after injection of nontargeted nanoparticles, by either the $H_f$ or $I_f$(1.99) receivers are shown, in the top and bottom panels of FIG. 7.

The value of 1.99 was chosen after an initial round of numerical experimentation to assess numerical stability of receiver output (while also varying the number of terms required for the Fourier series reconstruction of $\rho_f(y)$, versus computation time. However, in embodiments, a value greater than 1.0 and less than or equal to two may be used. As the goal is ultimately to develop an algorithm of clinical utility, the execution time of one week required to compute the $I_f$(1.99) images for this study was taken as an upper acceptable bound. Comparison of the data in FIG. 6 and FIG. 7 show that $I_f$(1.99) is able to detect accumulation of targeted nanoparticles in only half the time (post-injection) required by $H_f$. Pharmacokinetic dynamics would lead us to expect the steady increase of targeted nanoparticles in the region of insonification post-injection. Both plots of FIG. 6 are consistent with this model, however, $I_f$(1.99) may be more sensitive to their presence than $H_f$.

Previous studies have also shown:

$$H_f = \int_{f_{min}}^{f_{max}} \rho_f(y) \log[\rho_f(y)] dy, \quad (9)$$

can be more sensitive to subtle changes in scattering architecture than are more commonly used energy-based measures with subsequent studies demonstrating further sensitivity improvements using $I_f$ at the suitable value of $r^1$. For the density functions $\rho_f(y)$ encountered in a study, $I_f(r)$ is undefined for $r \geq 2$, since as $r \to 2^-$, the integral appearing in Equation (8) may grow without bound due to the singularities in the density function, $\rho_f(y)$ described in Equation (6). The behavior as $r \to 2$ is dominated by contributions from these singularities, all of which correspond to critical points of f(t). This behavior is shown in the left panel of FIG. 4. Moreover, as shown in the right panel it is possible that two slightly different functions, f(t) and f(t)+ξ(t), where ξ(t) is small, may have entropies, $H_f$ and $H_{f+\xi}$ that are close, as shown, but whose Renyi entropies, $I_f(r)$ and $I_{f+\xi}(r)$ diverge as $r \to 2$. Previous results have shown that this can happen in practice.

Figure 8:
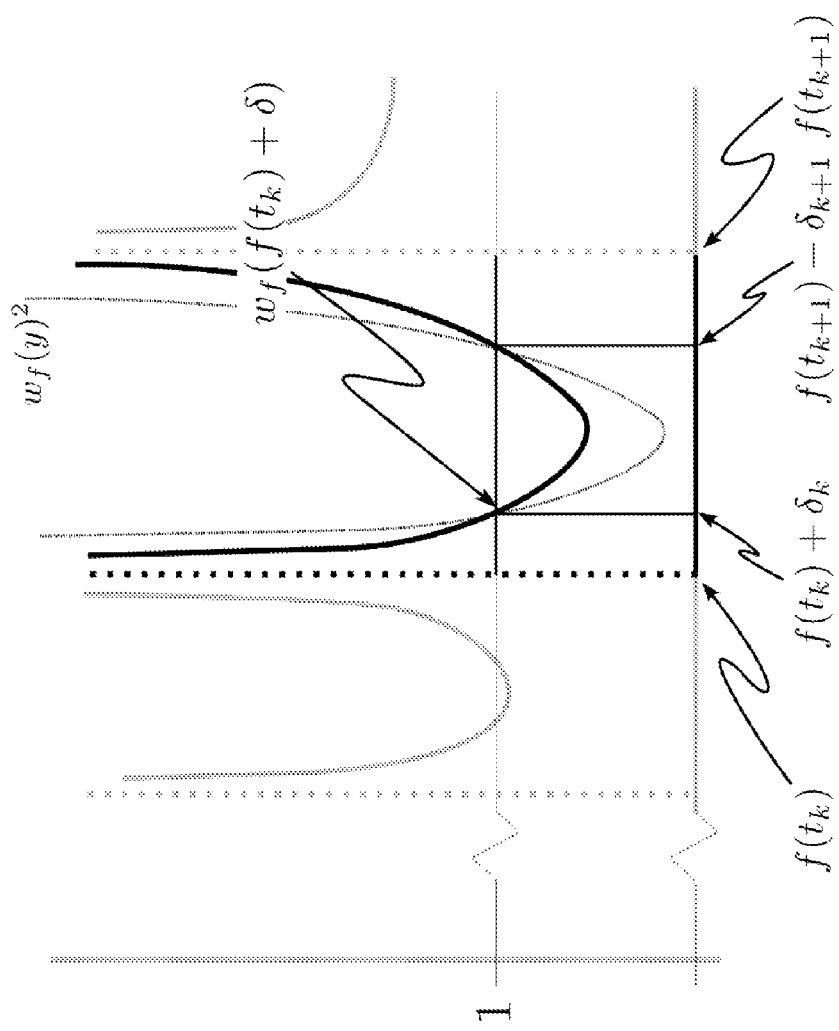
FIG. 8 illustrates an enlarged plot of a singularity of the density function $w_f(y)$.

The present disclosure establishes an upper bound on what is attainable by pushing toward this limit. In embodiments, to do this, the limiting form of $I_f(r)$ as $r \to 2$, is utilized, which will now be derived. First, it may only be necessary to consider small intervals around the singularities of, $\rho_f(y)$. The singularity corresponding to the $k^{th}$ minima if f(t), f($t_k$) is shown in FIG. 8, also shown is the adjacent singularity corresponding to a maxima of f(t), $t_{k+1}$. A dashed line indicates a plot of $w_f(y)^2$. Because $w_f(f(t_k))$ is infinite, there exists a $\delta_k>0$ such that $\rho_f(f(t_k)+\delta_k)=1$, as shown in FIG. 4. While the contribution to the integral in Equation (8) from the interval $[f(t_k)+\delta_k, f(t_k)-\delta_{k+1}]$ is bounded by $f(t_{k+1})-\delta_{k+1}-f(t_k)-\delta_k$ as $r \to 2$, the contribution from the interval $[f(t_k) \cdot f(t_k)+\delta]$ grows without bound.

By Equation (2), for y near $f(t_k)$, a significant contribution from $\rho_f(y)$ may come from values of t near $t_k$. Thus, near $y=f(t_k)$, $\rho_f(y)$ behaves locally like the density function for the parabolic fit to f(t) near $t_k$, which is given by Equation (4). Thus, the asymptotic form (assuming a minima, the argument for a maxima is similar) is obtained:

$$\rho_f(y) \sim \frac{a_k}{\sqrt{y - f(t_k)}} \quad (14)$$

where $\alpha_k = \sqrt{2/f''(t_k)} = \sqrt{2/|f''(t_k)|}$ i.e., Equation (6). The contribution to Equation (8) from all minima is the sum:

$$\lim_{\epsilon \to 0} \sum_{\substack{k \\ f''(t_k)>0}} \int_{f(t_k)}^{f(t_k)+\delta} \left(\frac{a_k}{\sqrt{y - f(t_k)}}\right)^{2-\epsilon} dy = \quad (15)$$

$$= \lim_{\epsilon \to 0} \sum_{\substack{k \\ f''(t_k)>0}} a_k^{2-\epsilon} \int_{f(t_k)}^{f(t_k)+\delta} (y - f(t_k))^{1-\epsilon/2} dy,$$

$$= \lim_{\epsilon \to 0} \sum_{\substack{k \\ f''(t_k)>0}} a_k^{2-\epsilon} \frac{(y - f(t_k))^{\epsilon/2}}{\epsilon/2} \Big|_{f(t_k)}^{f(t_k)+\delta},$$

$$= \lim_{\epsilon \to 0} \sum_{\substack{k \\ f''(t_k)>0}} a_k^{2-\epsilon} \frac{(f(t_k) + \delta - f(t_k))^{\epsilon/2}}{\epsilon/2},$$

$$= \lim_{\epsilon \to 0} \sum_{\substack{k \\ f''(t_k)>0}} \frac{2a_k^2}{\epsilon},$$

independent of δ and computable directly from the experimentally accessible function $f(t)$. Aside: for the maxima, the asymptotic term is present:

$$\lim_{\epsilon \to 0} \int_{f(t_k)-\delta_k}^{f(t_k)} \left(\left(\frac{a_k}{\sqrt{f(t_k) - y}}\right)\right)^{2-\epsilon} dy. \quad (16)$$

so that the contribution to Equation (8) from all of the maxima becomes:

$$= \lim_{\epsilon \to 0} \sum_{\substack{k \\ f''(t_k)<0}} \int_{f(t_k)-\delta_k}^{f(t_k)} \left(\frac{a_k}{\sqrt{f(t_k) - y}}\right)^{2-\epsilon} dy. \quad (17)$$

-continued $$= \lim_{\epsilon \to 0} \sum_{\substack{k \\ f''(t_k)<0}} a_k^{2-\epsilon} \int_{f(t_k)-\delta_k}^{f(t_k)} (f(t_k)-y)^{1-\epsilon/2} dy,$$

$$= \lim_{\epsilon \to 0} \sum_{\substack{k \\ f''(t_k)<0}} a_k^{2-\epsilon} \frac{(f(t_k)-y)^{\epsilon/2}}{\epsilon/2} \bigg|_{f(t_k)-\delta_k}^{f(t_k)},$$

$$= \lim_{\epsilon \to 0} \sum_{\substack{k \\ f''(t_k)<0}} a_k^{2-\epsilon} \frac{(f(t_k)-f(t_k)+\delta_k)^{\epsilon/2}}{\epsilon/2},$$

$$= \lim_{\epsilon \to 0} \sum_{\substack{k \\ f''(t_k)<0}} \frac{2a_k^2}{\epsilon},$$

where now a different expression for $\alpha_k = \alpha_k = \sqrt{-2/f''(t_k)} = \sqrt{2/|f''(t_k)|}$.

Adding the contribution for the maxima and minima:

$$\lim_{\epsilon \to 2} \int_{f_{min}}^{f_{max}} w_f(y)^r dy = = \lim_{\epsilon \to 0} \sum_{\{t_k | f'(t_k)=0\}} \frac{2a_k^2}{\epsilon}, \quad (18)$$

$$= \lim_{\epsilon \to 0} \sum_{\{t_k | f'(t_k)=0\}} \frac{4}{\epsilon |f''(t_k)|},$$

$$= \lim_{\epsilon \to 0} \frac{4}{\epsilon} \sum_{\{t_k | f'(t_k)=0\}} \frac{1}{|f''(t_k)|},$$

substituting this into Equation (8), $$\lim_{\epsilon \to 0} I_f(2-\epsilon) = -\log\left[\sum_{\{t_k | f'(t_k)=0\}} \frac{1}{|f''(t_k)|}\right] + \log 4 - \log \epsilon \quad (19)$$

In embodiments, for imaging applications, where offset removal and rescaling are typically performed when pixel values are assigned, the new quantity is defined:

$$I_{f,\infty} \equiv -\lim_{\epsilon \to 0} I_f(2-\epsilon) - \log 4 + \log \epsilon \quad (20)$$

$$= \log\left[\sum_{\{t_k | f'(t_k)=0\}} \frac{1}{|f''(t_k)|}\right].$$

A calculation may be accomplished by fitting a cubic spline to the experimentally acquired data array using a well-known algorithm, which returns the second derivative of the cubic spline (in an array having the same length as the experimental data) and initializes data structures suitable for rapid computation of its first derivative. Subsequently, an array of corresponding first derivatives may be computed used to bracket the critical points of the spline. Linear interpolation may be used to estimate the exact location of the bracketed zero crossings in order to obtain an algorithm suitable for real-time implementation in a medical imaging system.

The convergence properties, stability in the presence of noise, and effects of quantization error have been extensively evaluated using simulated data. Several types of waveforms have been investigated: Gaussians and parabolic waveforms, for which the exact value may be computed and linear combinations of exponentially damped sine waves that qualitatively resemble backscattered ultrasonic waveforms.

In embodiments, the effects of noise may be mitigated by two factors: the second derivative is obtained from a global fit to the data, the second derivative appears in the denominator of the expression for receiver output so that values of second derivative having large error are likely to make small contributions to the sum appearing in Equation (20).

In embodiments, histogram analysis was also performed using 85%, 87%, 90%, 91%, 93%, 95%, and 97% percent thresholds, with 93 percent having the best statistical separation between time points. The mean value of pixels classified as "targeted" may be computed at each time post-injection.

Figure 9:
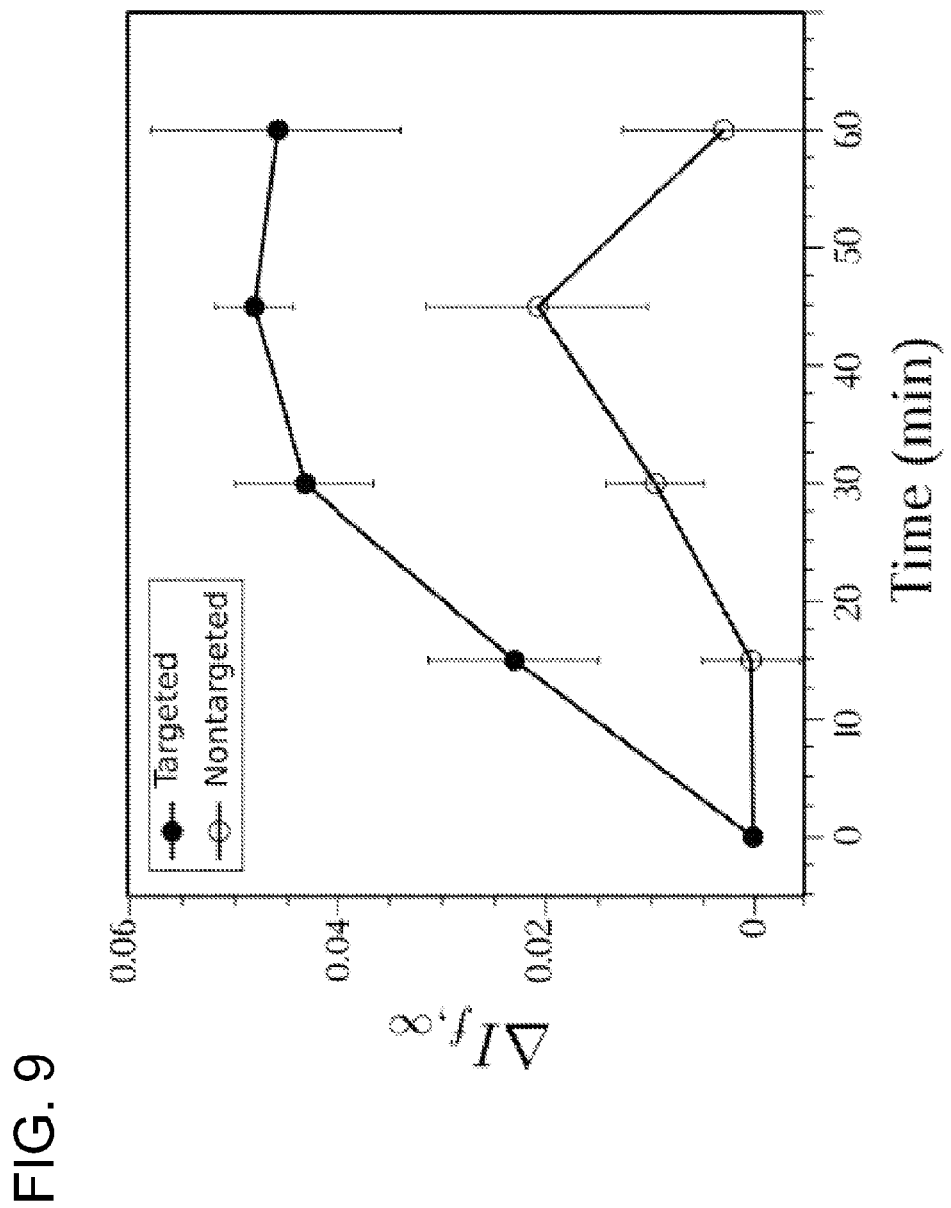
FIG. 9 illustrates the results obtained after injection of targeted nanoparticles and nontargeted nanoparticles by $I_{f\infty}$ receiver.

The results obtained after injection of targeted nanoparticles and nontargeted nanoparticles by $I_{f,\infty}$ receiver, are shown in FIG. 9. Both curves show the time evolution of the change (relative to 0 minutes) in mean value of receiver output in the enhanced regions of images obtained from the four animals in the targeted and the four animals in the non-targeted groups. Standard error bars are shown with each point. At fifteen minutes, the change in mean value if $I_{f,\infty}$ is more than two standard errors from zero, implying a statistical significant at the 95% level. However, there is no statistically significant change in image brightness for the nontargeted nanoparticles group. As the results show, the algorithm for computation of $I_{f,\infty}$ is stable in the presence of experimental noise.

The results presented in the present disclosure are a continuation of earlier studies where it was shown that an entropy based measure, $H_f$, was able to detect targeted nanoparticles in tumor neovasculature after 30 minutes of accumulation time. Subsequently, the required accumulation time was reduced to 15 minutes using a generalization of entropy, $I_f(r)$, with r=1.99, although the time required for signal analysis was greatly increased. In the current study, based on $I_{f,\infty}$ analysis time has been reduced using an algorithm suitable to real-time implementation, while maintaining sensitivity that permits detection of nanoparticle accumulation at 15 minutes.

Real-time performance appears to have been purchased at the price of reduced statistical sensitivity, $I_f(1.99)$ separated by over five standard errors from 0 at 15 minutes as compared to the 2 standard error separation from 0 obtained with the real-time receiver. It is possible that preprocessing of the data by bandpass filtering might improve the statistical performance of the algorithm without significant increase in computational overhead.

In a further example, a dystrophinopathies includes a group of X-linked genetic diseases that feature dystrophin deficiency. Duchenne and Becker muscular dystrophy are characterized by progressive weakness and wasting of skeletal, smooth, and/or cardiac muscle. Duchenne's Muscular Dystrophy (DMD) is the most severe dystrophinopathy, and with an incidence of 1:3500 male births. Despite understanding the structural and genetic basis for DMD, the pathogenesis and clinical basis for more severe involvement in specific skeletal muscle groups and the heart are poorly understood. Current techniques, such as strength testing, for monitoring progress of disease and therapy in DMD patients, are imprecise and physically demanding for test subjects. Ultrasound is well-suited to detect changes in structure and organization in muscle tissue in a manner that makes low demands on the patient. Therefore, the use of ultrasound to quantitatively phenotype the remodeling process in patients with DMD may be used.

Beam-formed RF data may be acquired from the skeletal muscles of nine DMD and five normal subjects imaged with a clinical imaging system (HDI5000 w/7 MHz probe applied above left biceps muscle). From these data, images may be reconstructed using B-mode (log of analytic signal magnitude) and information-theoretic receivers ($H_f$-receivers). $H_f$ images obtained from dystrophic muscle may contain extensive "mottled" regions (i.e. areas with heterogeneous image contrast) that are not readily apparent from the B-Mode images. The two dimensional autocorrelation of DMD $H_f$ images may have broader peaks than those of normal subjects, which is indicative of larger scatterer sizes, consistent with pathological changes of fibers, edema, and fatty infiltration. Comparison of the relative peak widths (full width measured at 60% maximum) of the autocorrelation of the DMD and normal $H_f$ images may show a quantitative difference between the two groups (p<0.005). Thus, these imaging techniques prove useful for longitudinal monitoring of disease progression and therapy. In embodiments, these same signal analysis may be performed using $I_f(1.99)$ and $I_{f,\infty}$, instead of $H_f$.

Figure 10A:
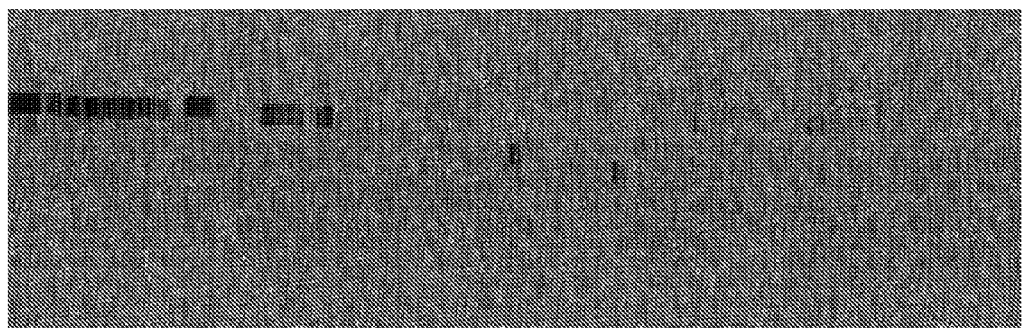
FIGS. 10A and 10B illustrate the results with a Renyi index equal to −1.00 and equal to 1.99.
Figure 10B:
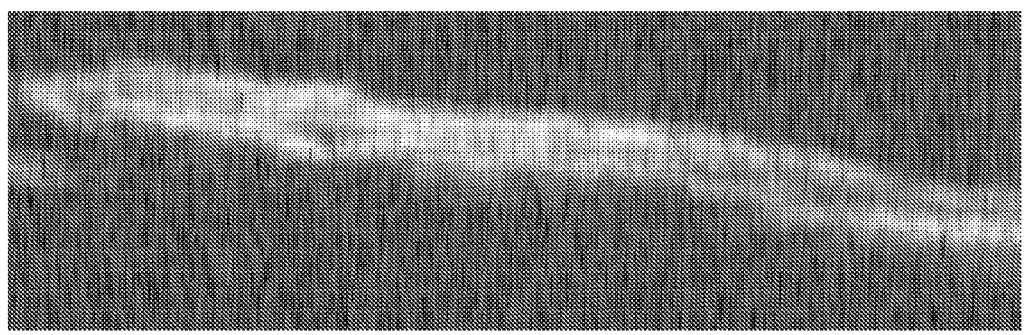

FIG. 10A and FIG. 10B illustrate the results with a Renyi index equal to −1.00 and equal to 1.99, respectively.

Figure 11:
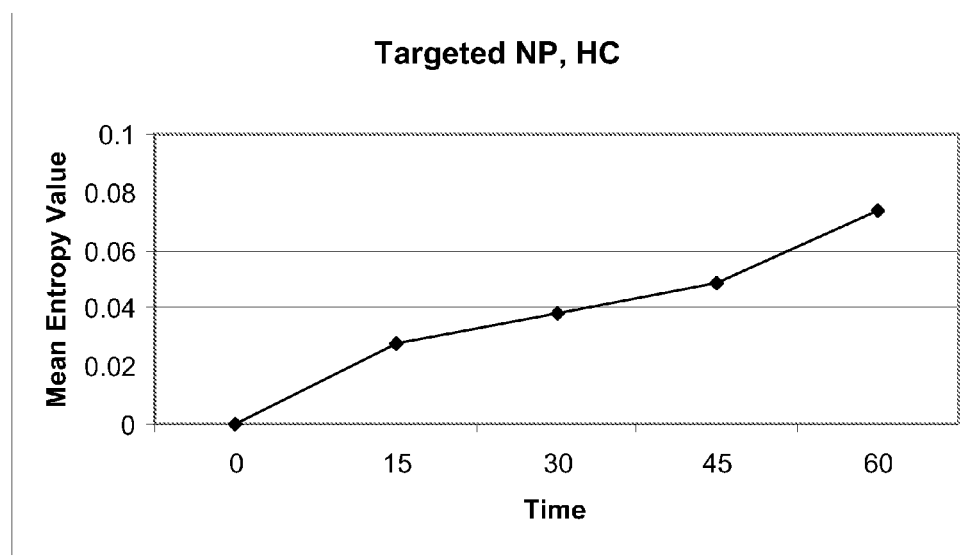
FIG. 11 illustrates targeted mean entropy values over time.

FIG. 11 illustrates targeted mean entropy values over time. In FIG. 11, the relevant P-values include 0.0224 at 0 versus 60, 0.0456 at 0 versus 30, 0.0628 at 0 versus 15, and 0.0725 at 15 versus 60.

Figure 12:
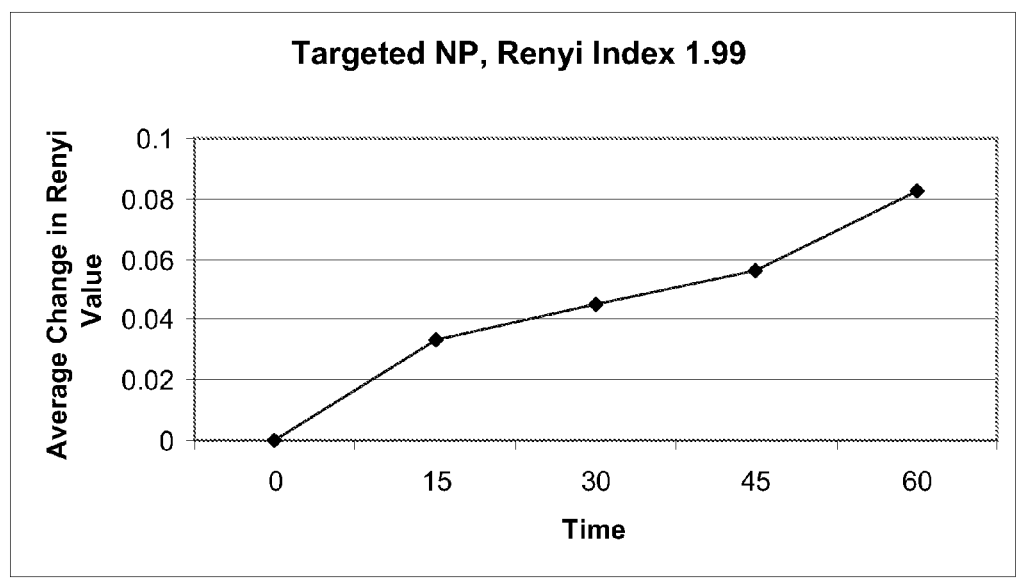
FIG. 12 illustrates targeted average change in Renyi values over time.

FIG. 12 illustrates targeted average change in Renyi values over time. In FIG. 11, the relevant P-values include 0.00897 at 0 versus 60, 0.02637 at 0 versus 30, 0.01257 at 0 versus 15, and 0.0295 at 15 versus 60.

Figure 13:
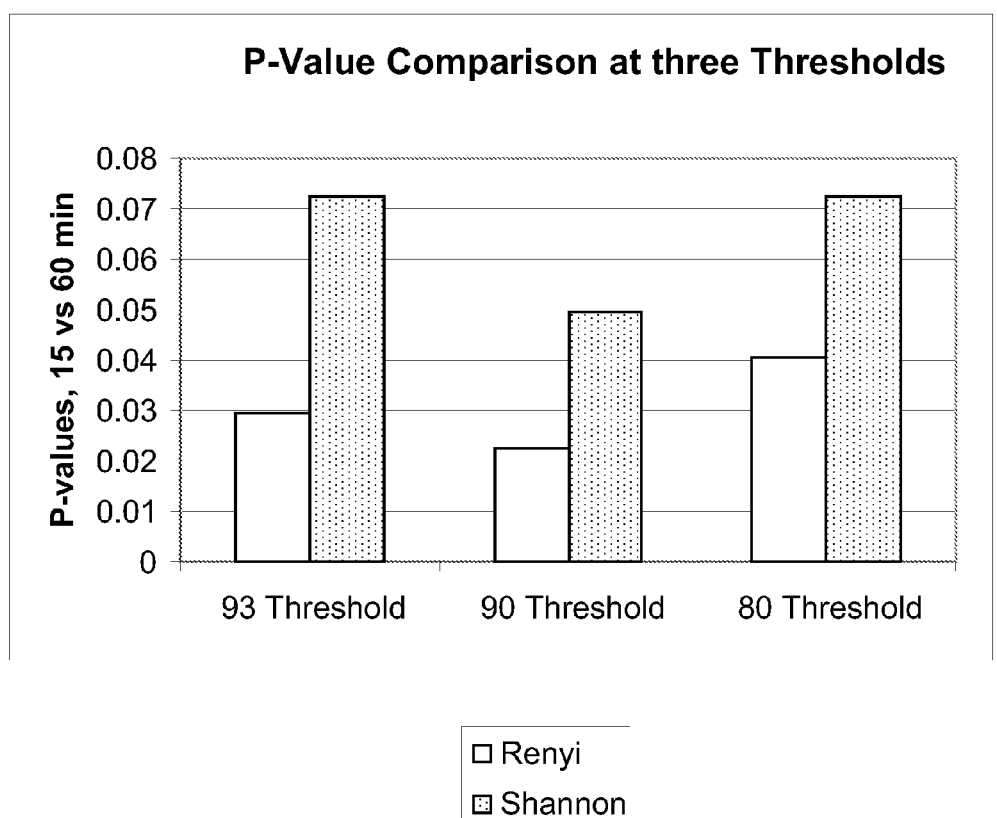
FIG. 13 illustrates a P-value comparison at three thresholds.

FIG. 13 illustrates a P-value comparison at three thresholds.

Figure 14A:
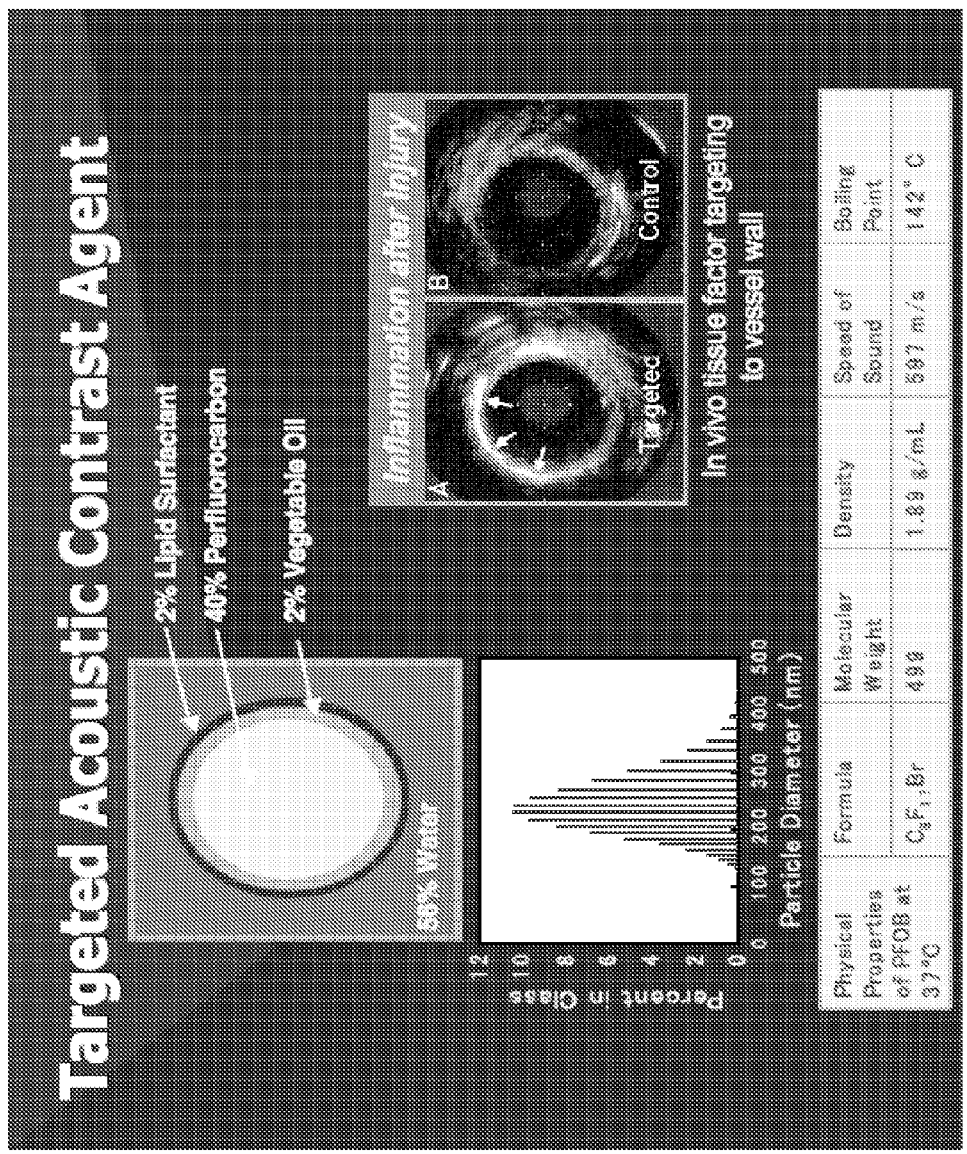
FIG. 14A illustrates targeted acoustic contrast agents.

FIG. 14A illustrates targeted acoustic contrast agents.

Figure 14B:
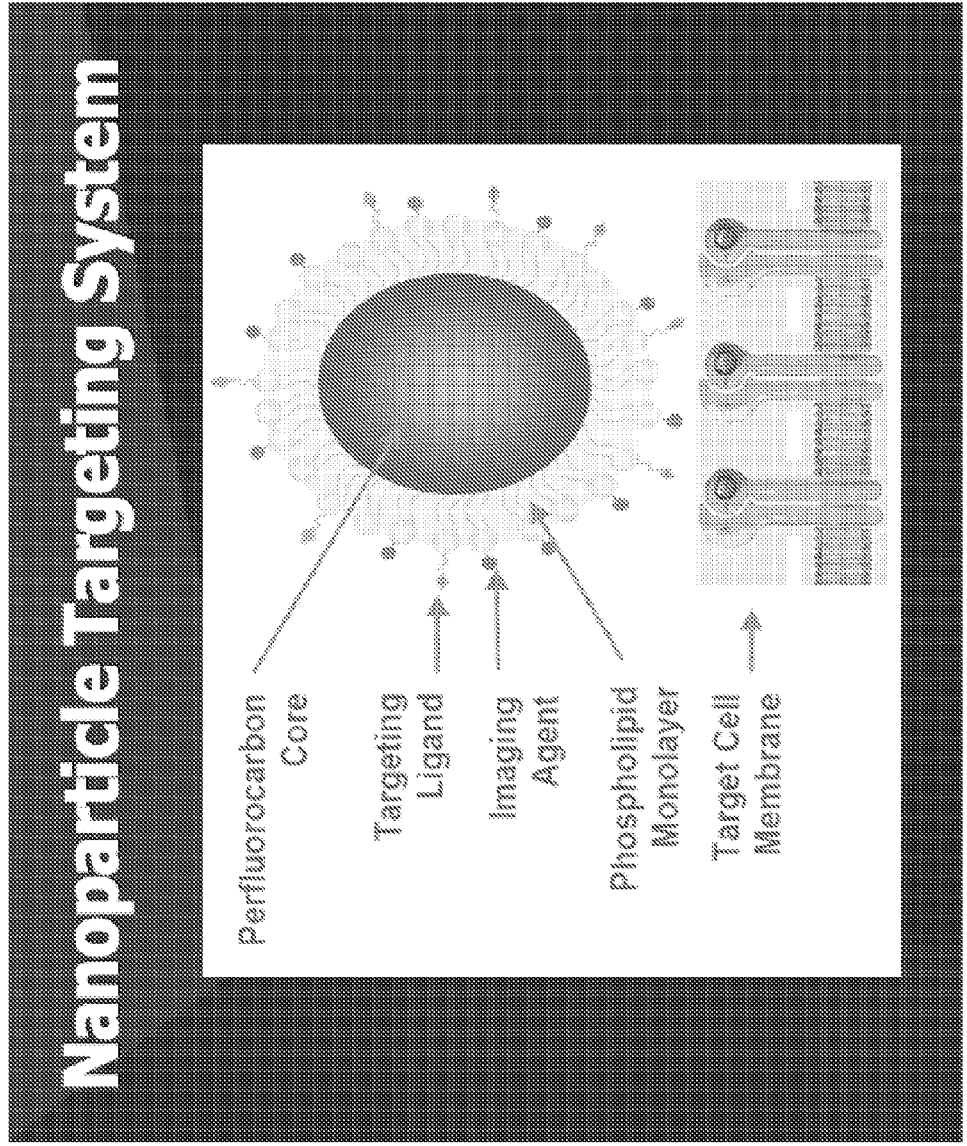
FIG. 14B illustrates a nanoparticle targeting system.

FIG. 14B illustrates a nanoparticle targeting system.

Figure 15:
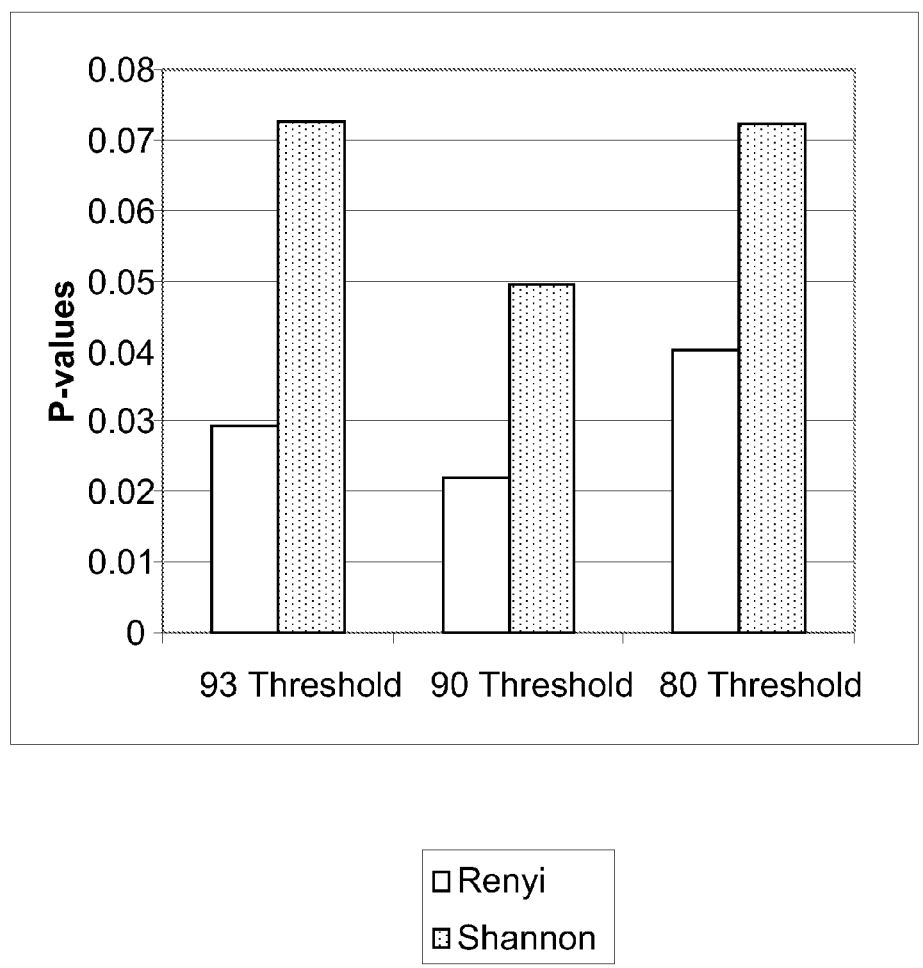
FIG. 15 illustrates a comparison of P values for Renyi and Shannon entropy values at various thresholds.

FIG. 15 illustrates a comparison of P values for Renyi and Shannon entropy values at various thresholds.

Exemplary Operating Environment

A computing device such as computer used herein with respect to FIG. 1 has one or more processors or processing units and a system memory. The computer typically has at least some form of computer readable media. Computer readable media, which include both volatile and nonvolatile media, removable and non-removable media, may be any available medium that may be accessed by computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information and that may be accessed by computer. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of any of the above are also included within the scope of computer readable media.

The system memory includes computer storage media in the form of removable and/or non-removable, volatile and/or nonvolatile memory. The computer may operate in a networked environment using logical connections to one or more remote computers, such as a remote computer.

Although described in connection with an exemplary computing system environment, embodiments of the disclosure are operational with numerous other general purpose or special purpose computing system environments or configurations. The computing system environment is not intended to suggest any limitation as to the scope of use or functionality of any aspect of the disclosure. Moreover, the computing system environment should not be interpreted as having any dependency or requirement relating to any one or combination of components illustrated in the exemplary operating environment. Examples of well known computing systems, environments, and/or configurations that may be suitable for use with aspects of the disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the disclosure may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein. Aspects of the disclosure may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the disclosure described and/or illustrated herein.

The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

This written description uses examples to disclose the claimed subject matter, including the best mode, and also to enable any person skilled in the art to practice the claimed subject matter, including making and using any devices or systems and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for imaging a region of interest (ROI) within a body, the method comprising:
    applying ultrasound energy to the ROI;
    receiving ultrasound data for the ROI in response to the applied ultrasound energy;
    executing a moving window analysis on the received ultrasound data to generate a plurality of windows of information;
    applying a Renyi entropy signal receiver to each of the generated windows to generate Renyi entropy data, wherein the Renyi entropy signal receiver is defined as:

$$I_f(r) = \frac{1}{1-r} \log \left[ \int_{f_{min}}^{f_{max}} \rho_f(y)^r dy \right],$$

wherein $\rho_f(y)$ defines a density function of a signal f(t), wherein $f_{min}$ is a minimum of f(t) and $f_{max}$ is a maximum of f(t), and wherein r is an adjustable parameter; and
    presenting an image of the ROI based on the Renyi entropy data.

2. The method of claim 1, wherein the image of the ROI data is indicative of whether a condition of interest exists.

3. The method of claim 2, wherein the condition of interest comprises tissue affected by cancer.

4. The method of claim 1, further comprising injecting the ROI with a contrast agent that is targeted to a condition of interest.

5. A method for imaging a region of interest (ROI) within a body, the method comprising:
    applying ultrasound energy to the ROI;
    receiving ultrasound data for the ROI in response to the applied ultrasound energy;
    executing a moving window analysis on the received ultrasound data to generate a plurality of windows of information;
    applying a $I_{f,\infty}$ entropy signal receiver to each of the generated windows to generate Renyi entropy data; and
    presenting an image of the ROI based on the $I_{f,\infty}$ entropy data.

6. The method of claim 5, further comprising defining the $I_{f,\infty}$ entropy signal receiver to be $$I_{f,\infty} = \log \left[ \sum_{\{t_k | f'(t_k)=0\}} \frac{1}{|f''(t_k)|} \right].$$

7. The method of claim 5, wherein the image of the ROI data is indicative of whether a condition of interest exists.

8. The method of claim 7, wherein the condition of interest comprises tissue affected by cancer.

9. The method of claim 5, further comprising injecting the ROI with a contrast agent that is targeted to a condition of interest.

10. An ultrasound imaging system, comprising:
    an ultrasound transducer configured to apply an acoustic signal to a region of interest (ROI) in a body, and transform a reflection of the applied acoustic signal into a raw radio frequency waveform;
    an analog-to-digital converter (ADC) configured to generate a digitized waveform of the raw radio frequency waveform; and
    a processor configured compute pixel values from the digitized waveform, wherein a display device is configured to present an image of the ROI based on the pixel values, wherein the processor includes a Renyi entropy signal receiver configured to generate Renyi entropy data, wherein the Renyi entropy signal receiver is defined as:

$$I_f(r) = \frac{1}{1-r} \log \left[ \int_{f_{min}}^{f_{max}} \rho_f(y)^r dy \right],$$

wherein $\rho_f(y)$ defines a density function of a signal f(t), wherein $f_{min}$ is a minimum of f(t) and $f_{max}$ is a maximum of f(t), and wherein r is an adjustable parameter.

11. The ultrasound imaging system in accordance with claim 10, wherein computing pixel values from the digitized waveform comprises performing a moving window analysis of each digitized waveform.

12. The ultrasound imaging system in accordance with claim 11, wherein the performing the moving window analysis of said digitized waveform comprises iteratively selecting a defined plurality of consecutive points to generate a window position until each of the points in the digitized waveform has been included in a window.

13. The ultrasound imaging system in accordance with claim 12, wherein the moving window analysis comprises:
    receiving values for each defined plurality of consecutive points at each window position;
    inputting the received values for each window position into the Renyi entropy signal receiver; and
    computing datum for each window position, wherein the datum serves as a pixel in a resulting image.

14. The ultrasound imaging system in accordance with claim 10, wherein the ultrasound transducer is further configured to sense and/or receive the reflection of the applied acoustic signal prior to transforming the reflection of the applied acoustic signal into said raw radio frequency waveform.

15. The ultrasound imaging system in accordance with claim 10, wherein the ADC is further configured to sample the raw radio frequency waveform at a predefined sample rate to generate the digitized raw radio frequency waveform.

16. The ultrasound imaging system in accordance with claim 15, wherein the predefined sample rate is about 500 MHz.

17. The ultrasound imaging system in accordance with claim 10, wherein the digitized waveform comprises a plurality of frames, each of which comprises a plurality of lines of numerous multi-bit words.

18. The ultrasound imaging system in accordance with claim 10, wherein each of the plurality of frames corresponds spatially to an area within the ROI.

* * * * *